(12) United States Patent
Castaneda et al.

(10) Patent No.: US 10,603,130 B2
(45) Date of Patent: Mar. 31, 2020

(54) MEASUREMENT DEVICE AND METHOD FOR HEADLESS ORTHOPAEDIC COMPRESSION SCREWS

(71) Applicant: Biomet Manufacturing, LLC, Warsaw, IN (US)

(72) Inventors: Alfredo Castaneda, Miami, FL (US); Michael Gellatly, Miami Springs, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 845 days.

(21) Appl. No.: 15/046,953

(22) Filed: Feb. 18, 2016

(65) Prior Publication Data

US 2016/0242832 A1 Aug. 25, 2016

Related U.S. Application Data

(60) Provisional application No. 62/118,166, filed on Feb. 19, 2015.

(51) Int. Cl.
| | | |
|---|---|---|
| *A61B 17/88* | (2006.01) | |
| *A61B 90/00* | (2016.01) | |
| *A61B 17/86* | (2006.01) | |
| *A61B 17/68* | (2006.01) | |

(52) U.S. Cl.
CPC .......... *A61B 90/06* (2016.02); *A61B 17/8645* (2013.01); *A61B 2017/681* (2013.01); *A61B 2090/061* (2016.02); *A61B 2090/062* (2016.02); *A61B 2090/3966* (2016.02)

(58) Field of Classification Search
CPC ... A61C 19/04; A61B 90/06; A61B 2090/061; A61B 2090/062; A61B 5/1072; A61B 5/1076; A61B 5/1077
USPC .................................. 606/102, 104; 33/836
See application file for complete search history.

(56) References Cited

U.S. PATENT DOCUMENTS

| | | | | |
|---|---|---|---|---|
| 4,204,548 A | * | 5/1980 | Kurz ...................... | A61B 1/303 600/591 |
| 4,362,167 A | * | 12/1982 | Nicolai .................... | G01B 3/46 33/512 |
| 4,383,527 A | * | 5/1983 | Asnis ................. | A61B 17/1721 606/96 |
| 5,013,318 A | * | 5/1991 | Spranza, III ......... | A61B 5/1076 33/512 |
| 5,197,465 A | * | 3/1993 | Montgomery .... | A61M 16/0472 128/200.26 |
| 6,013,081 A | * | 1/2000 | Burkinshaw ......... | A61B 17/155 606/102 |

(Continued)

*Primary Examiner* — Anu Ramana
(74) *Attorney, Agent, or Firm* — Schwegman Lundberg & Woessner, P.A.

(57) ABSTRACT

Disclosed is an orthopedic measurement device. The orthopedic measurement device can comprise a tip section, a backend section, and a middle section. The tip section can have a distal end sized to fit into a hole drilled into a bone. The middle section can be located between the tip section and the backend section. The middle section can include a plurality of measurement features. Each of the plurality of measurement features can be a fixed distance from the distal end of the tip section. The middle section can be sized to fit into the hole drilled into the bone. The tip section, the backend section, and the middle section can define a cannula sized to receive a wire.

19 Claims, 3 Drawing Sheets

(56) References Cited

U.S. PATENT DOCUMENTS 8,572,860 B2 * 11/2013 Fritzinger .............. A61B 90/06
33/512
9,421,049 B2 * 8/2016 Rogachefsky ..... A61B 17/7291

* cited by examiner

MEASUREMENT DEVICE AND METHOD FOR HEADLESS ORTHOPAEDIC COMPRESSION SCREWS

PRIORITY APPLICATIONS

This application claims the benefit of priority to U.S. Provisional Application Ser. No. 62/118,166, filed Feb. 19, 2015, the content of which is incorporated herein by reference in its entirety.

FIELD OF THE INVENTION

The present invention relates to orthopedic screws, and more particularly, to headless orthopedic compression screws.

BACKGROUND

A common site of orthopedic trauma in humans occurs in the hands, due in part to the natural reflex to put one's hands out during a fall to absorb the impact of the fall. Of the bones in the hand, the scaphoid is commonly fractured during these traumatic events due to its location within the hand. To repair scaphoid fractures, compression screws can be utilized to compress and hold the bone fragments together while the body's natural healing process fuses the fragments back together.

One particular type of compression screw that is commonly used to hold scaphoid bone fragments together is a headless compression screw. As opposed to traditional compression screws, the headless compression screws forego the head portion of the screw, which is typically formed at one end of the screw and compresses on the cortical shell of the scaphoid to compress the fragments together. By using headless compression screws rather than traditional compression screws, the entirety of the compression screw can rest inside the cancellous bone of the scaphoid as the bone heals.

Since the entire compression screw rests within the scaphoid when using a headless compression screw, the length of the headless compression screw is of utmost importance to the success of the repair procedure. If the screw is too long, a portion of the screw will rest outside of the cancellous bone and may stick out past the outer surface of the scaphoid, which can cause damage to surrounding soft tissues. If the screw is too short, the screw will not achieve sufficient purchase within the cancellous bone to hold the bone fragments together, which can allow for the bone fragments to separate from each other and render the screw useless. To overcome this problem, various methods and devices have been utilized to attempt to allow a user to select the proper headless compression screw length.

One such method involves placing a Kirschner wire (k-wire) within the scaphoid across the scaphoid's length and sliding a depth gage over the k-wire until the tip of the depth gage touches the outer surface of the bone. The depth gage therefore measures the entire length that the k-wire has penetrated into the scaphoid, with a predetermined value being subtracted from the measurement to come up with the screw length that should be used. A second method to determine the length of the compression screw involves placing a k-wire within the scaphoid, similar to the first method, and then pressing a second k-wire of equal length against the outer surface of the scaphoid adjacent to the entry hole of the first k-wire. The k-wires are then aligned so that a measurement can be taken to determine the length difference between the k-wires, which should approximate the length of the first k-wire that is in the scaphoid.

The current practice is to select a screw for implantation that is 2 to 4 millimeters shorter than the measured distance, to account for various difficulties associated with measurement of the scaphoid such as the asymmetrical nature of the scaphoid, difficulty visualizing the screw's eventual placement within the scaphoid, and the fragments typically being separated when the measurement is taken. This practice of "selecting short" can lead to a compression screw being selected that is too short and many users complain that the current practice makes it difficult to precisely select the proper headless compression screw length.

What is needed in the art is a device and method for selecting the appropriate length of a headless compression screw to hold scaphoid bone fragments together that gives more consistent and accurate measurements than known devices and methods.

SUMMARY

To better illustrate the orthopedic compression screws and devices disclosed herein, a non-limiting list of examples is provided here:

In Example 1, an orthopedic measurement device can comprise a tip section, a backend section, and a middle section. The tip section can have a distal end sized to fit into a hole drilled into a bone. The middle section can be located between the tip section and the backend section. The middle section can include a plurality of measurement features. Each of the plurality of measurement features can be a fixed distance from the distal end of the tip section. The middle section can be sized to fit into the hole drilled into the bone. The tip section, the backend section, and the middle section can define a cannula sized to receive a wire.

In Example 2, the orthopedic measurement device of Example 1 can optionally include the tip section and the middle section being formed from a radiopaque material.

In Example 3, the orthopedic measurement device of any one of or any combination of Examples 1 and 2 can optionally include the tip section having a substantially solid outer surface.

In Example 4, the orthopedic measurement device of any one of or any combination of Examples 1-3 can optionally include the plurality of measurement features comprise notches on an outer surface of the middle section.

In Example 5, the orthopedic measurement device of Example 4 can optionally include the notches having a width of at least 0.2 millimeters.

In Example 6, the orthopedic measurement device of any one of or any combination of Examples 1-5 can optionally include the plurality of measurement features spanning a range of about 1 millimeter to about 3 millimeters.

In Example 7, the orthopedic measurement device of any one of or any combination of Examples 1-6 can optionally include the tip section having a length of between about 12 millimeters and about 16 millimeters.

In Example 8, the orthopedic measurement device of any one of or any combination of Examples 1-7 can optionally include the tip section and the middle section having a stiffness such that the middle section and the tip section do not experience a length deformation greater than about 20% during use.

In Example 9, an orthopedic measurement system comprise a device body and a wire. The device body can define a longitudinal axis having a first end and a second end. The device body can define a cannula formed along the longitudinal axis. The cannula can extend from the first end toward the second end. The device body can include a tip section, a backend section, and a middle section. The tip section can define the first end. The backend section can define the second end. The middle section can be located between the tip section and the backend section. The middle section can include a plurality of measurement features. Each of the plurality of measurement features spaced from at least one neighboring measurement feature by a measurement distance. The wire can be sized to fit into the cannula.

In Example 10, the orthopedic measurement system of Example 9 can optionally include the device body being formed from a radiopaque material.

In Example 11, the orthopedic measurement system of any one of or any combination of Examples 9 and 10 can optionally include the device body being formed from a radiolucent material and the plurality of measurement features being formed from a radiopaque material.

In Example 12, the orthopedic measurement system of any one of or any combination of Examples 9-11 can optionally include the plurality of measurement features comprise notches having a width of at least 0.2 millimeters.

In Example 13, the orthopedic measurement system of any one of or any combination of Examples 9-12 can optionally include the plurality of measurement features spanning a range of about 1 millimeter to about 3 millimeters.

In Example 14, the orthopedic measurement system of any one of or any combination of Examples 9-13 can optionally include the tip section having a length of between about 12 millimeters and about 16 millimeters.

In Example 15, the orthopedic measurement system of any one of or any combination of Examples 9-14 can optionally include the tip section and the middle section having a stiffness such that the middle section and the tip section do not experience a length deformation greater than about 20% during use.

In Example 16, the orthopedic measurement system of any one of or any combination of Examples 9-15 can optionally include a compression element configured to compress a plurality of bone segments during a measurement procedure.

In Example 17, the orthopedic measurement system of any one of or any combination of Examples 9-16 can optionally include a plurality of headless screws of various lengths. The tip section can have a length corresponding to the shortest of the plurality of headless screws.

In Example 18, a method for measuring for a headless compression screw can comprise: drilling a hole through a first bone segment and into a second bone segment; attaching a wire to the second bone segment; inserting an orthopedic measurement device into the hole through the first bone segment and into the second bone segment; and obtaining a measurement from the plurality of measurement features. The wire can pass through the hole in the first bone segment. The orthopedic measurement device can include a tip section, a backend section, and a middle section that define a cannula. The cannula can be sized to allow the wire to pass at least partially through the orthopedic measurement device. The middle section can include a plurality of measurement features located a fixed distance from a distal end of the tip section. The measurement can correspond to a headless compression screw of a given length.

In Example 19, obtaining the measurement of Example 18 can optionally include x-raying the first bone segment and the second bone segment while the orthopedic measurement device is inserted into the hole drilled through the first bone segment and into the second bone segment.

In Example 20, the method of any one of or any combination of Examples 18 and 19 can optionally include the middle section being formed from a radiolucent material and the plurality of measurement features being formed from a radiopaque material.

In Example 21, the orthopedic measurement device, the orthopedic measurement system, and the method of any one of or any combination of Examples 1-20 is optionally configured such that all elements or options recited are available to use or select from.

DESCRIPTION OF THE FIGURES

The above-mentioned and other features and advantages of this invention, and the manner of attaining them, will become more apparent and the invention itself will be better understood by reference to the following description of examples of the invention taken in conjunction with the accompanying drawings, wherein.

Corresponding reference characters indicate corresponding parts throughout the several views. The exemplifications set out herein illustrate examples of the invention, and such exemplifications are not to be construed as limiting the scope of the invention any manner.

DESCRIPTION OF THE INVENTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves.

Figure 1:
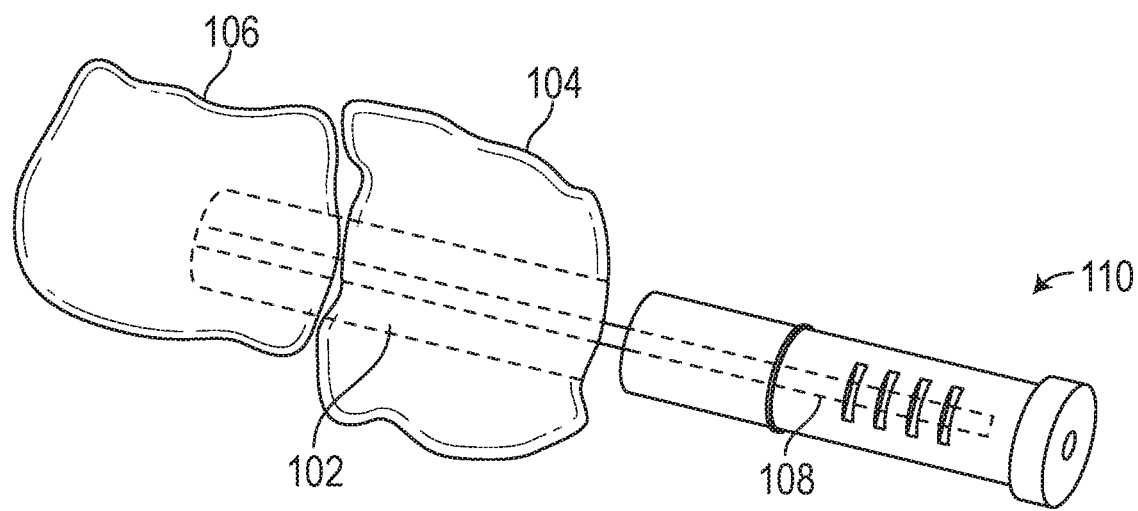
FIG. 1 shows an example operating environment for measuring headless compression screws in accordance with at least one example of the present disclosure.

Referring now to the figures, FIG. 1 shows an example operating environment for measuring headless compression screws in accordance with at least one example of the present disclosure. As shown in FIG. 1, during a measurement procedure, a hole 102 can be drilled through a first bone segment 104 and terminate in a second bone segment 106. A wire 108 can pass through the first bone segment 104 and be secured to the second bone segment 106. An orthopedic measurement device 110 can pass over the wire 108 and be inserted into the first bone segment 104 and the second bone segment 106. As described herein, once the orthopedic measurement device 110 is inserted into the bone segments, a measurement can be made to determine an appropriate length of a headless compression screw.

Figure 2A:
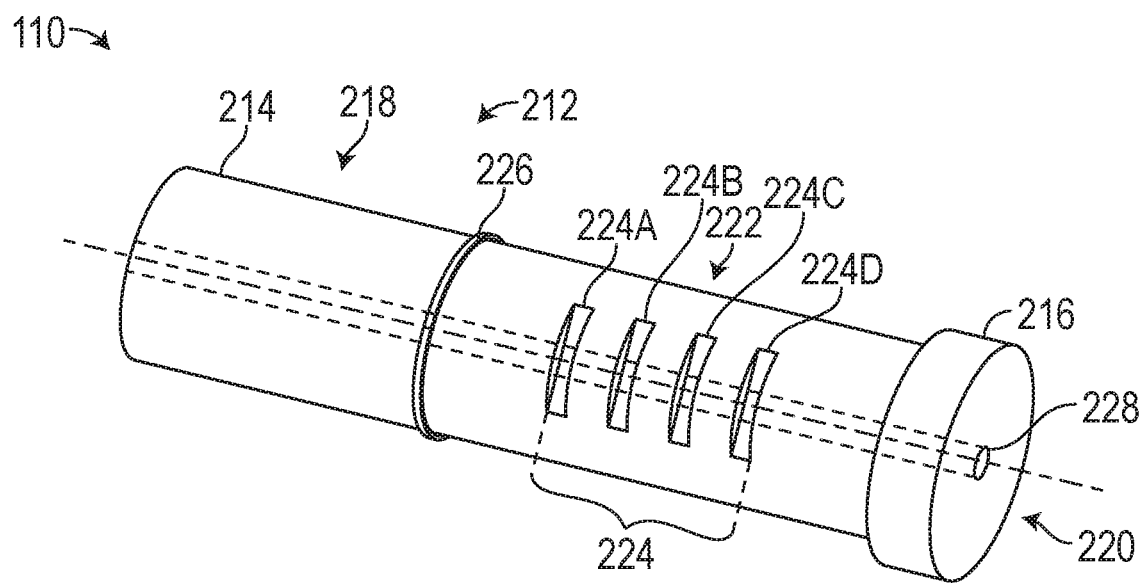
FIGS. 2A-2C show example perspective, front, and side views of a measurement device for a headless orthopedic compression screw in accordance with at least one example of the present disclosure.
Figure 2B:
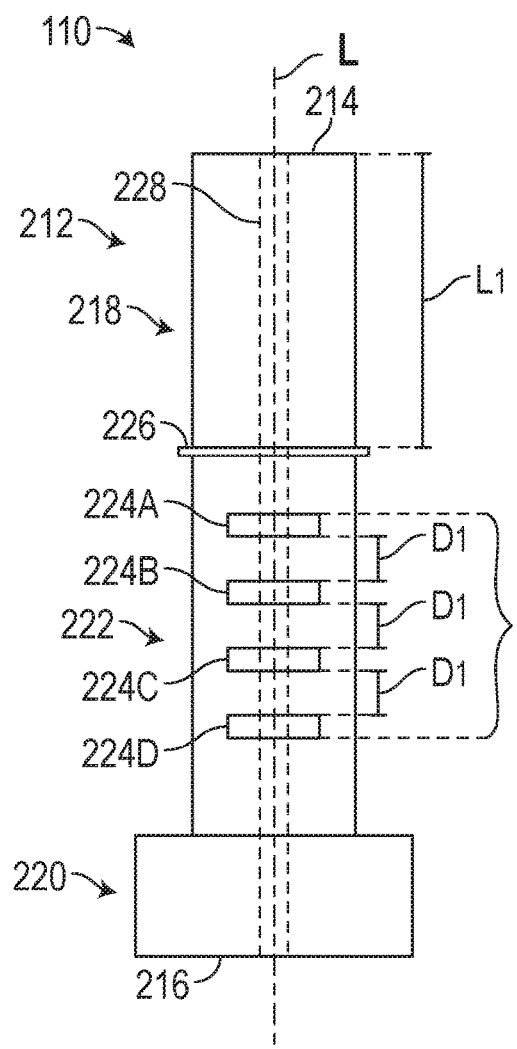
Figure 2C:
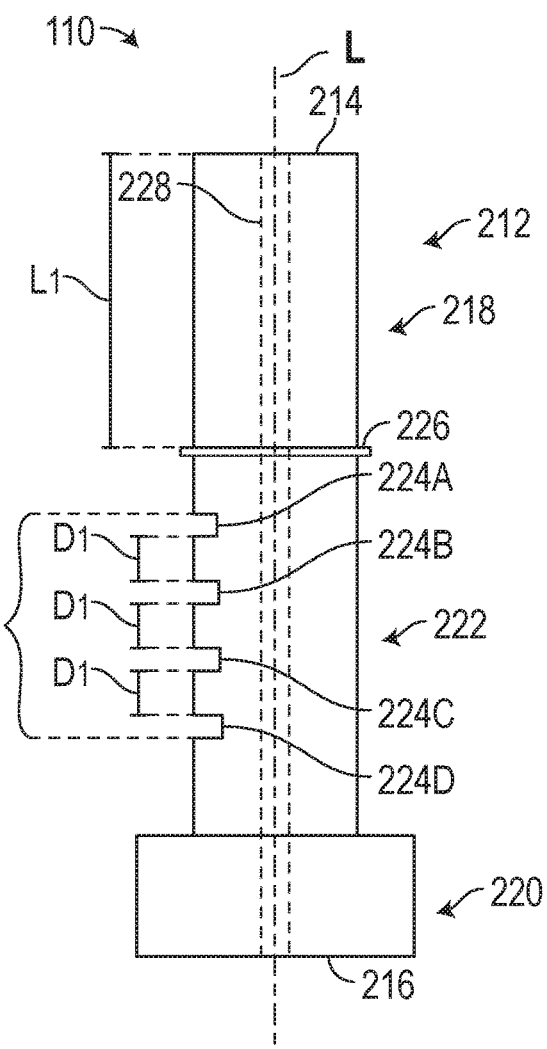

FIGS. 2A-2C show an embodiment of the orthopedic measurement device 110 in accordance with at least one example of the present disclosure. The orthopedic measurement device 110 can include a device body 212. The body device 212 can define a longitudinal axis L, a first end 214 and a second end 216. As shown in FIGS. 2A-2C, a cannula 228 can be formed in the device body 212. The cannula 228 can extend along the longitudinal axis L from the first end 214 toward the second end 216. The cannula 228 can be formed as a generally circular opening with a diameter that is sufficiently large to allow the orthopedic measurement device 110 to slide over commonly used k-wires. The cannula 228 can extend continuously from the first end 214 to the second end 216. In addition, the cannula 228 can extend a portion of the way from the first end 214 toward the second end 216 such that a k-wire cannot completely pass through the orthopedic measurement device 110.

The device body 212 can include three distinct sections: a tip section 218 defined adjacent to the first end 214, a backend section 220 formed adjacent to the second end 216, and a middle section 222 defined between the tip section 218 and the backend section 220. As shown, the device body 212 can be a single unit with each section 218, 220, 222 formed as an integral part of the device body 212. In addition, one or more of the sections 218, 220, 222 can be separable from the other sections to allow for customization of the orthopedic measurement device 110. The device body 212, and therefore sections 218, 220 and 222, can be fully or partially formed from a radiopaque material to allow for easy visualization of the orthopedic measurement device 110 using non-invasive imaging techniques, such as fluoroscopy.

As used herein, "radiopaque" refers to a material property allowing for the material to be visualized using X-rays. Stated another way, a radiopaque material will be visible when using X-ray imaging. Non-limiting examples of radiopaque materials include titanium, stainless steel, and doped polymers which are known to be radiopaque.

During use, the orthopedic measurement device 110 can encounter bodily fluids and living tissue. Thus, the device body 212 can be formed from a biocompatible material that can exhibit surgically acceptable levels of cytotoxicity. The device body 212 also can be formed from a material that can be sterilized after use. As a result, the orthopedic measurement device 110 can be reused in multiple surgeries. In addition, the orthopedic measurement device 110 can be disposable and intended for use during a single surgery.

As shown in FIGS. 2A-2C, the tip section 218 can be formed adjacent to the first end 214 of the device body 212 and can have a tip length L1. During use, the tip section 218 can be the section of the device body 21 that is first inserted into an anatomical structure (e.g., a human hand) of a patient. The tip length L1 can therefore be adjusted to correspond to a shortest possible length of a headless compression screw that can be used. Example tip lengths L1 can be from approximately 14 to 16 millimeters. The lengths can vary to account for standard tolerances.

To provide strength to the device body 212 as it is being inserted, the tip section 218 can be a solid section surrounding the cannula 228 formed through the device body 212. In addition, the device body 212 can have a substantially solid outer surface that does not have material removed therefrom. Furthermore, the tip section 218 can have various cutting features such as teeth or flutes to aid in the insertion of the measurement device 110 into the anatomical structure. The flutes or other external structures can aid in holding the orthopedic measurement device 110 within the anatomical structure.

The tip section 218 can be shaped as a cannulated cylinder. The overall diameter of the cannulated cylinder, or tip section 218, can be chosen to allow the tip section 218 to be inserted into a drilled hole that s formed in the anatomical body during the surgical procedure. For example, a surgeon may drill a hole having a first diameter and select a tip section 218 that has a second diameter. The first diameter may be larger than the second diameter.

The backend section 220 can be formed adjacent to the second end 216 of the device body 212. During use, the backend section 220 can remain outside of a fractured bone being measured using the orthopedic measurement device 110. As shown in FIGS. 2A-2C, the backend section 220 can be significantly wider than the tip section 218 and middle section 222. The backend section can have an ergonomic shape that can provide an easy to grip portion of the orthopedic measurement device 110.

During use the backend section 220 may not need to be visualized using imagining techniques, e.g., X-rays, during a surgical procedure. As a result, the backend section 220 can be formed from radiolucent materials. Use of radiolucent materials can lead to lowering the cost of producing the orthopedic measurement device 110 or provide a more ergonomic gripping portion. The backend section 220 can be formed from radiopaque materials as detailed above.

If the device body 212 is not formed as a single piece, the backend section 220 can be securely attached to the middle section 222 to provide sufficient stiffness to maneuver the tip section 218 and middle section 222 to their proper location during use.

A compression element 226 can be placed on the backend section 222 or between the backend section 222 and tip section 218. The compression element 226 can compress bone fragments together while the orthopedic measurement device 110 is being used. A non-limiting example of the compression element 226 that can be used is a washer. The washer can be disposed around the middle section 220, which can be independently movable relative to the tip section 218. Thus, when the tip section 218 is held within a bone, such as a scaphoid, or bone fragments, the compression element 226 can be pressed into one of the fragments to compress the fragments together before taking a measurement. The resulting measurement would therefore correspond to the compressed length of the hone fragments. This can eliminate the need to subtract a distance from the chosen compression screw to account for the compression of the bone fragments that will occur during placement of the screw.

The compression element 222 can be formed of any biocompatible material. In addition, the compression element can be radiopaque or radiolucent. The position of the compression element 222 along the orthopedic measurement device 110 can be adjustable. For example and as shown in the figures, the compression element can be located at a joint formed by the tip section 218 and the middle section 222.

The middle section 222 can be formed between the tip section 218 and the backend section 220 of the device body 212. The middle section 222 can include a plurality of measurement features 224. As shown FIGS. 2A-2C, the measurement features 224 can be formed as cuts, notches, or other indentations in an outer surface of the middle section 222. The measurement features can be readily visible under fluoroscopy when the middle section 222 is formed from a radiopaque material and the cuts or notches have a sufficient width. For example, when the widths of cuts, notches, or other indentations in the outer surface of the middle section 222 are at least 0.2 millimeters, they can be visible using standard mini C-Arm fluoroscopy equipment. Widths smaller or larger than 0.2 millimeters can also be chosen, if desired. The widths can be designed and optimized such that the middle section 222 and tip section 218 do not materially affect the stiffness so as to compromise the length measurement during use. For instance, the tip section 222 and the middle section 222 can have a stiffness such that the middle section 222 and tip section 218 do not experience 20% or more length deformation of the tip section 218 and middle section 222. In addition, the widths of the cuts, notches, or other indentations can be designed and optimized such that they remain large enough to be readily visualized under fluoroscopy.

If the middle section 222 is formed from a radiolucent material, the measurement features 224 can be formed as radiopaque bands that extend around the middle section 222 and can be visible under fluoroscopy. As such, it should be appreciated that a variety of measurement features 224 can be included in or on the middle section 222 so long as the measurement features 224 are somehow visually distinguishable from the rest of the middle section 222 to the naked eye and/or when imaged using X-rays.

The measurement features 224 can be spaced apart such that a measurement distance D1 is formed between neighboring measurement features 224. As can be seen in FIGS. 2A-2C, there can be four measurement features 224, shown as notches cut into the middle section 222, that can each be roughly spaced apart from neighboring measurement features 224 by the measurement distance D1. For ease of description, the individual measurement features are labelled as measurement feature 224A defining a border of the tip section 218 and middle section 222. A measurement feature 224B can be spaced by the measurement distance D1 from the measurement feature 224A along the longitudinal axis L toward the backend section 220, a measurement feature 224C can be spaced by the measurement distance D1 from measurement feature 224B, and a measurement feature 224D can be spaced by the measurement distance D1 from measurement feature 224C. Assuming that the measurement distance is 2 millimeters, for example, measurement feature 224B is 2 millimeters from measurement feature 224A, measurement feature 224C is 4 millimeters from measurement feature 224A, and measurement feature 224D is 6 millimeters from measurement feature 224A. In this sense, the measurement features 224 allow a user to measure the distance of each particular measurement feature 224A, 224B, 224C and 224D from the tip section 218. While the measurement features 224A, 224B, 224C, and 224D are shown as having only one measurement distance D1 between neighboring measurement features, the distance between neighboring measurement features can vary along the length of the middle section 222. Additionally, although four measurement features 224A, 224B, 24C, and 224D are shown, any number of measurement features can be utilized.

During use the orthopedic measurement device 110, a bone to be repaired, such as a scaphoid, can be exposed so that a hole can be drilled in the bone across bone fragments using a drill or other cutting means, such as a medical power drill. Once the hole is drilled, a k-wire can be inserted into the hole. The hole can extend along the length of the bone across the bone fragments so that an implanted compression screw can access sufficient cancellous bone tissue to achieve enough purchase within the bone to resist pull out and provide sufficient compression. Once the k-wire is inserted in the hole, the area can be visualized using fluoroscopy so that the surgeon can verify whether the hole has the desired location and length. After verifying the k-wire's positioning, the surgeon can slide the first end 214 of the device body 212 over the k-wire so that the orthopedic measurement device 110 can be advanced into the hole.

The diameter of the hole can be larger than the diameter of the tip section 218 and the middle section 222 such that the tip section 218 and the middle section 222 can be inserted into the hole. The orthopedic measurement device 110 can be inserted into the hole until the first end 214 contacts a distal end of the hole. The distal end of the hole can be within cancellous bone of the distal bone fragment. Optionally, the compression element 226 can be deployed to compress the proximal and distal bone fragments together such that a length of the measurement takes into account the compression that can occur once the headless compression screw is implanted across the proximal and distal bone fragments.

Once properly placed in the hole, the tip section 218 and middle section 222 can be visualized under fluoroscopy to determine a length of a headless compression screw to be used. Since the first end 214 can be in contact with the distal end of the hole, the length of the device body 212 that is held within the hole can directly correspond to a length of the hole. The tip length L1 of the tip section 218 can provide a known length. For example, the tip section 218 can have a tip length L1 that can correspond to the shortest possible headless compression screw intended to be used in conjunction with the orthopedic measurement device 110. The measurement features 224 can provide relative distances from the tip section 218. For example, the measurement feature 224A can define the border of the tip section 218 and be located at an amount equal to the tip length L1 from the first end 214, measurement feature 224B can be 2 millimeters from the tip section 218, measurement feature 224C can be 4 millimeters from the tip section 218, and measurement feature 224D can be 6 millimeters from the tip section 218.

In an example, assuming the tip length L1 is 16 millimeters, the surgeon can fluoroscopically visualize the location of one of the measurement features 224 within the formed hole where the surgeon desires the proximal end of the headless compression screw to be after implantation. Upon visualization, the surgeon can determine a length of the headless compression screw based on the measurement feature's distance from the tip section. For example, if the measurement device 110 is inserted in the hole and the surgeon sees on the fluoroscopy monitor that measurement feature 224C is located where the proximal end of the headless compression screw should rest after implantation, the surgeon can determine that the headless compression screw should be 220 millimeters long based on the tip length L1 being 16 millimeters and measurement feature 224C being 4 millimeters from the tip section 218.

In this sense, the surgeon does not need to estimate how much distance to add or subtract from the measurement because there can be direct visualization that allows the surgeon to see where the proximal end of the headless compression screw will ultimately be fixed after implantation. As disclosed herein, the middle section 222 can include measurement features 224 that are spaced from each other to allow for a large number of direct measurements the proper headless compression screw length to be taken.

Figure 3A:
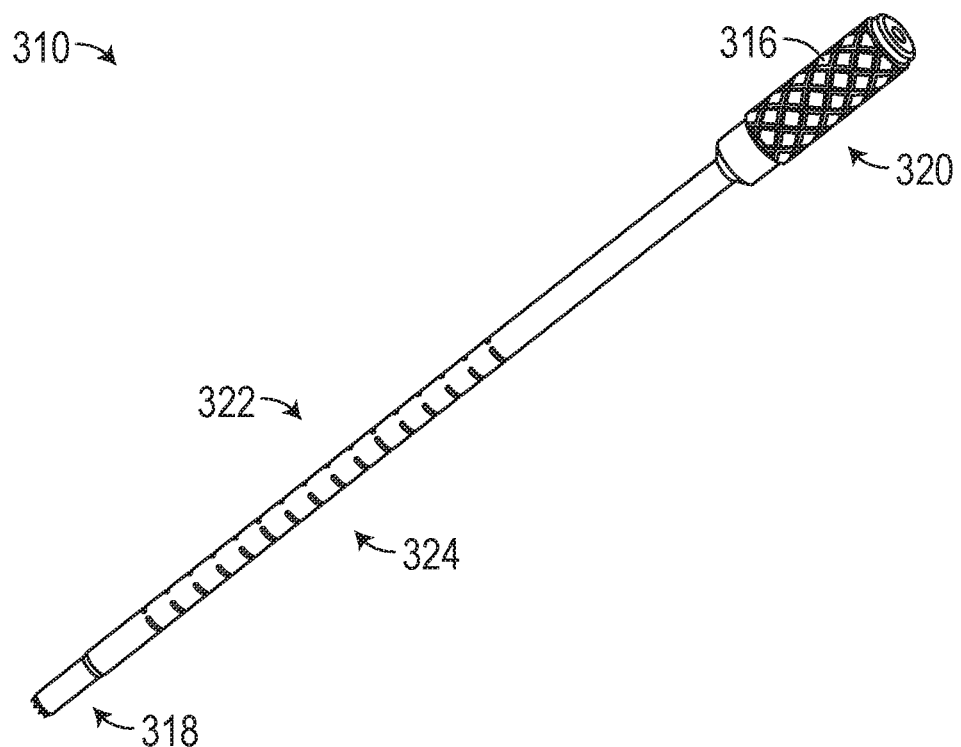
FIGS. 3A and 3B show example perspective and front views of a measurement device for a headless orthopedic compression screw in accordance with at least one example of the present disclosure.
Figure 3B:
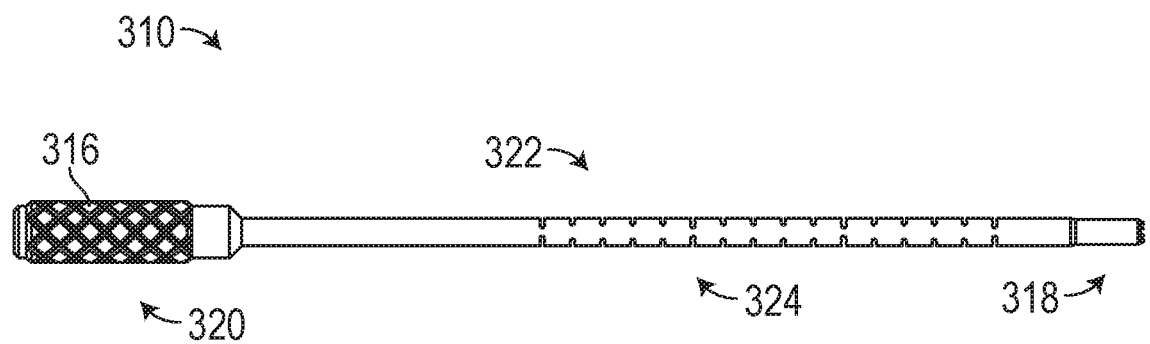

FIGS. 3A and 3B show an example measurement device 310 for a headless orthopedic compression screw in accordance with at least one example of the present disclosure. As shown in FIGS. 3A and 3B, the measurement device 310 can include a tip section 318, a backend section 320, and a middle section 322 located between the tip section 318 and the backend section 320. The backend section can include a textured surface 316. Surface elements of the textured surface 316 can include a uniform pattern (as shown) or a random pattern. The textured surface 316 can increase a tactile feel and allows for a more secure grip by a surgeon.

The middle section 322 can include a plurality of measurement features 324. As disclosed herein, the plurality of measurement features 324 can included notches, grooves, or other indentations that are spacing conducive to obtaining a measurement. In addition, as shown in FIGS. 3A and 3B, tip section 318, the middle section 322, and the backend section 320 can be of different lengths. Furthermore, the various components of the measurement device 310 can have different diameters. For example, as shown in FIGS. 3A and 3B, the middle section 322 can have a smaller diameter than the backend section 320 and the tip section 318 can have a smaller diameter than the middle section 322.

The various components of the measurement device 310 can be disassembled. For instance, the tip section 318 and the backend section 320 can be separated from the middle section 322. The separable nature can allow the measurement device 310 to be customized for a particular patient or particular surgery. For example, a longer middle section 322 can be used for larger bones, such as a femur or humerus, and a shorter middle section 322 can be used for smaller bones such as scaphoid, carpal bones, phalanges, etc.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. An orthopedic measurement device comprising:
   a tip section having a distal end sized to fit into a hole drilled into a plurality of bone segments;
   a backend section;
   a middle section located between the tip section and the backend section, the middle section including a plurality of measurement features, each of the plurality of measurement features being a fixed distance from the distal end of the tip section, the middle section sized to fit into the hole drilled into the plurality of bone segments, wherein the tip section, the backend section, and the middle section defining a single cannula along a longitudinal axis of the middle section and sized to receive a single wire attached to one of the plurality of bone segments; and
   a compression element slideably located on the middle section or tip section, the compression element configured to be pressed into a hole drilled into one of the plurality of bone segments so as to compress the plurality of bone segments together before a measurement procedure.

2. The orthopedic measurement device of claim 1, wherein the tip section and the middle section are formed from a radiopaque material.

3. The orthopedic measurement device of claim 1, wherein the tip section has a substantially solid outer surface.

4. The orthopedic measurement device of claim 1, wherein the plurality of measurement features comprise notches on an outer surface of the middle section.

5. The orthopedic measurement device of claim 4, wherein the notches have a width of at least 0.2 millimeters.

6. The orthopedic measurement device of claim 1, wherein the plurality of measurement features span a range of about 1 millimeter to about 3 millimeters.

7. The orthopedic measurement device of claim 1, wherein the tip section has a length of between about 12 millimeters and about 16 millimeters.

8. The orthopedic measurement device of claim 1, wherein the tip section and the middle section have a stiffness such that the middle section and the tip section do not experience a length deformation greater than about 20% during use.

9. An orthopedic measurement system comprising:
   a device body defining a longitudinal axis having a first end and a second end, the device body defining a single cannula formed along the longitudinal axis, the cannula extending from the first end toward the second end, the device body including:
     a tip section defining the first end, the tip section sized to fit into a hole drilled into a plurality of bone segments,
     a backend section defining the second end,
     a middle section located between the tip section and the backend section, the middle section sized to fit into the hole drilled into the plurality of bone segments, the middle section including a plurality of measurement features, each of the plurality of measurement features being spaced from at least one neighboring measurement feature by a measurement distance, and
     a compression element slideably located on the middle section or tip section, the compression element configured to be pressed into a hole drilled into one of the plurality of bone segments and compress the plurality of bone segments before a measurement procedure; and
   a wire sized to fit into the cannula and attach to one of the plurality of bone segments.

10. The orthopedic measurement system of claim 9, wherein the device body is formed from a radiopaque material.

11. The orthopedic measurement system of claim 9, wherein the device body is formed from a radiolucent material and the plurality of measurement features are formed from a radiopaque material.

12. The orthopedic measurement system of claim 9, wherein the plurality of measurement features comprise notches having a width of at least 0.2 millimeters.

13. The orthopedic measurement system of claim 9, wherein the plurality of measurement features span a range of about 1 millimeter to about 3 millimeters.

14. The orthopedic measurement system of claim 9, wherein the tip section has a length of between about 12 millimeters and about 16 millimeters.

15. The orthopedic measurement system of claim 9, wherein the tip section and the middle section have a stiffness such that the middle section and the tip section do not experience a length deformation greater than about 20% during use.

16. The orthopedic measurement system of claim 9, further comprising a plurality of headless screws of various lengths, wherein the tip section has a length corresponding to the shortest of the plurality of headless screws.

17. A method for measuring a length of a headless compression screw, the method comprising:
   drilling a hole through a first bone segment and into a second bone segment;
   attaching a wire to the second bone segment, the wire passing through the hole in the first bone segment;
   inserting an orthopedic measurement device into the hole through the first bone segment and into the second bone segment, the orthopedic measurement device including a tip section, a backend section, and a middle section that define a cannula sized to allow the wire to pass at least partially through the orthopedic measurement device, the middle section including a plurality of measurement features located a fixed distance and spaced at even intervals from a distal end of the tip section; and obtaining a depth measurement from the plurality of measurement features, the measurement corresponding to the length of the headless compression screw.

18. The method of claim 17, wherein obtaining the measurement includes x-raying the first bone segment and the second bone segment while the orthopedic measurement device is inserted into the hole drilled through the first bone segment and into the second bone segment.

19. The method of claim 18, wherein the middle section is formed from a radiolucent material and the plurality of measurement features are formed from a radiopaque material.

* * * * *